United States Patent [19]

Häfele

[11] Patent Number: 5,696,313

[45] Date of Patent: Dec. 9, 1997

[54] LAMBDA SENSOR WITH ELECTRIC HEATER

[76] Inventor: Edelbert Häfele, Albert-Einstein-Strasse 62, D-76223 Karlsruhe, Germany

[21] Appl. No.: 629,964

[22] Filed: Apr. 10, 1996

[30] Foreign Application Priority Data

Apr. 14, 1995 [DE] Germany .......................... 195 13 490.7

[51] Int. Cl.$^6$ .......................................................... G01N 7/00
[52] U.S. Cl. .......................................................... 73/23.31
[58] Field of Search ............................ 73/23.31, 23.32, 73/23.37, 23.21, 23.2, 31.03, 31.05; 123/688, 678, 681

[56] References Cited

U.S. PATENT DOCUMENTS

| | | | |
|---|---|---|---|
| 4,348,583 | 9/1982 | Bube et al. | 219/497 |
| 4,352,347 | 10/1982 | Osano et al. | 123/440 |
| 4,611,562 | 9/1986 | Nakano et al. | 73/23.32 |
| 4,715,343 | 12/1987 | Kinoshita | 73/23.32 |
| 4,803,866 | 2/1989 | Miki et al. | 73/23 |
| 4,985,126 | 1/1991 | Haefele et al. | 204/153.14 |
| 5,454,259 | 10/1995 | Ishii et al. | 73/23.32 |
| 5,462,040 | 10/1995 | Krebs et al. | 123/688 |
| 5,528,148 | 6/1996 | Rogers | 324/426 |
| 5,544,640 | 8/1996 | Thomas et al. | 73/23.32 |

FOREIGN PATENT DOCUMENTS

G 91 03 547.3
U1 7/1982 Germany .

OTHER PUBLICATIONS

Robert Bosch GmbH, *Automotive Handbook*, 3rd English Edition, pp. 425 & 482, ©1993, Stuttgart.

*Primary Examiner*—Michael Brock
*Assistant Examiner*—Jay L. Politzer

[57] ABSTRACT

A novel apparatus, for determining the concentration of gas components in exhaust gas from a motor vehicle, features a lambda sensor element, an electric heater thermally coupled to the sensor element, a control unit regulating application of voltage to the heater, and at least two voltage sources which can be alternatively applied to the heater, as commanded by the control unit.

22 Claims, 1 Drawing Sheet

LAMBDA SENSOR WITH ELECTRIC HEATER

CROSS-REFERENCE TO RELATED LITERATURE

*Automotive Handbook, 3rd English Ed.*, Robert Bosch GmbH, Stuttgart, Germany, 1993, pages 425 & 482.

FIELD OF THE INVENTION

The present invention relates generally to an apparatus for determining the concentration of gas components in exhaust gases from motor vehicles, including an electrically heated lambda sensor, and a method of operating an exhaust gas sensor including a faster warm-up to operating temperature than in the prior art.

BACKGROUND

Gas sensors, especially lambda sensors, have long been known. For example, German published patent application DE-OS 36 10 363 and corresponding U.S. Pat No. 4,985,126 show a lambda sensor with a tubular solid electrolyte, which has a separate electric heater. This heating is necessary to bring the solid electrolyte up to its operating temperature. Further, German utility model DE 91 03 547 U1 discloses a gas sensor in which an electrical resistance heater and an active sensor element are arranged on a common carrier or substrate, and the overall mass of the active region is kept small, in order to assure a fast warm-up. The warm-up of this sensor is about 10 seconds faster than that of the older lambda sensors, but the time required for warm-up even with this sensor is up to 20 seconds.

In the context of efforts to minimize the overall pollutant output of a motor vehicle during a predetermined test cycle, the cold-start phase assumes great importance. There are, indeed, electrically heatable catalytic converters which become effective immediately after a cold start. Trouble-free functioning of the three-way catalytic converter, however, does not presuppose a controlled warm-up phase with a rich or lean mixture, but rather a controlled warm-up phase in which the mixture fed to the combustion engine has a λ-value in the area of 1. In the time interval before effective operation of the exhaust gas sensor, the exhaust gas cleaning apparatus finds itself in an ineffective operating state, because the signals necessary for the control process are not yet available. Whenever this time is longer than a few seconds, the pollutant output in the first seconds of the cold-running phase of the combustion engine can exceed the complete permitted pollutant output for the test cycle, so that the fully operational exhaust gas cleaner can no longer lead to staying within the predetermined limit values. It is therefore necessary, to make the installed exhaust gas sensors operational within a fewer number of seconds.

SUMMARY OF THE INVENTION

It is therefore an object of the present invention, to provide an apparatus and a method for determining the concentration of gas components in exhaust gas of a motor vehicle, which already offers usable measurement results, about 5 seconds after a cold start.

Briefly, this is achieved by heating up the lambda sensor from ambient temperature to operating temperature quickly by applying a relatively high-voltage source to the sensor's associated electric heater, and subsequently maintaining operating temperature by application of a second, lower-voltage, source to the heater.

Due to the fact that, in an apparatus with two voltage sources, the heater can be supplied from a first voltage source or from a second voltage source, as specified by a control device, the warm-up of the exhaust gas sensor during the cold-start phase can be supplied from a different voltage source than the heating during the steady operation of the exhaust gas sensor. The first voltage source can be the unregulated generator/alternator voltage of the dynamo, tapped before the voltage regulator, and the second voltage source can be the on-board network of the motor vehicle tapped downstream of the voltage regulator.

It is also possible, upon reaching the operating temperature of the sensor, to limit the applied heating power, using a clocked voltage feed, to the value which is adequate to maintain the operating temperature of the exhaust gas sensor in a warm state. The nominal voltage of the second voltage source approximates, depending on the model of motor vehicle, for example, 13.6 V (12-volt installations) or 27.2 V (24-volt installations). In the future, other on-board networks with other nominal voltages are of course possible.

If the voltage of the first voltage source is at least 30% above the nominal voltage of the second voltage source, a particularly quick heating of the sensor element is possible, since the preheating electrical power applied rises quadratically with the increase in voltage. One can advantageously use, as the first voltage source, the generator/alternator of the motor vehicle, since tapping upstream of the voltage regulator results in about double the usual on-board network voltage of the motor vehicle.

Immediately after the cold start, the heating device of the exhaust gas sensor is connected to the first voltage source, in order to supply the heating device with sufficient electrical power. Upon reaching operating temperature, the heating device is preferably connected to the second voltage source, which, with lower electrical power, supplies the voltage necessary to maintain operating temperature. One could also provide that the first voltage source is continued to be used for heating, but that heating power applied is reduced by clocking or pulsing the current fed.

The switchover from the first voltage source to the second voltage source can be carried out, in particularly simple fashion, as a function of time elapsed since the cold start. A reliable switchover, particularly in connection with very high electrical power, results if the switchover is carried out as a function of the temperature of the heating device. One can employ, as an indicator for the temperature of the sensor element, the current drawn by the heating device, since its electrical resistance depends upon the temperature reached.

A good temperature tolerance, and a reproducible dependence of electrical resistance upon temperature, are achievable if the heating device has a heating conductor which consists essentially of a platinum group metal, i.e. platinum, ruthenium, rhodium, palladium, osmium, iridium, or an alloy of the foregoing "Group VIII" metals. The warm-up of the sensor element occurs particularly quickly if the heating device and the sensor element are arranged on a common substrate. A heating device with a heating conductor, whose electrical resistance climbs as temperature increases, has the advantage that, at cold ambient temperature, and thus low starting temperature, the electrical heating power applied is high. The colder the sensor is at the start, the more strongly it is heated up.

Equally, the object of fast warm-up is achieved, in a motor vehicle having a combustion engine and an exhaust gas sensor with an associated heater, by initially applying a high voltage source to the heater to bring the sensor up to operating temperature, and subsequently applying a lower-voltage source, to maintain the sensor at operating temperature.

Since, after the start of the engine, the heating device of the exhaust gas sensor can be supplied initially from the first voltage source having higher nominal voltage and subsequently from the second voltage source having lower nominal voltage, a fast warm-up of the sensor element can be achieved initially, while the electrical power required to maintain the operating temperature is lower and can be applied from the second voltage source having lower nominal voltage. Depending upon the particular installation, one may be able to entirely omit a further electrical heating of the sensor, e.g. when the exhaust gas temperature is so high that, during operation, the sensor maintains a sufficient operating temperature without electrical heating.

It is particularly advantageous if the switchover from the first voltage source to the second voltage source is carried out between 2.5 and 20 seconds after a cold start. In the case of particularly high electrical heating power, it can even be advantageous for the switchover to be carried out between 1 second and 2.5 seconds after a cold start. According to another configuration, the switchover can be carried out between 3 seconds and 10 seconds after a cold start. The method can be advantageously arranged so that the determination of the instant for the switchover from the first voltage source to the second voltage source is a function of the current drawn by the heater.

BRIEF FIGURE DESCRIPTION

In the following, a preferred embodiment of the apparatus of the invention, and one of the method of the invention, are explained with reference to the drawings, in which:

FIG. 1 shows an exhaust gas sensor for use in the apparatus of the invention, including a sensor element and a heating element arranged commonly on a single substrate; and FIG. 2 is a schematic circuit diagram of the electrical circuitry of the exhaust gas sensor of FIG. 1.

DETAILED DESCRIPTION

Figure 1:
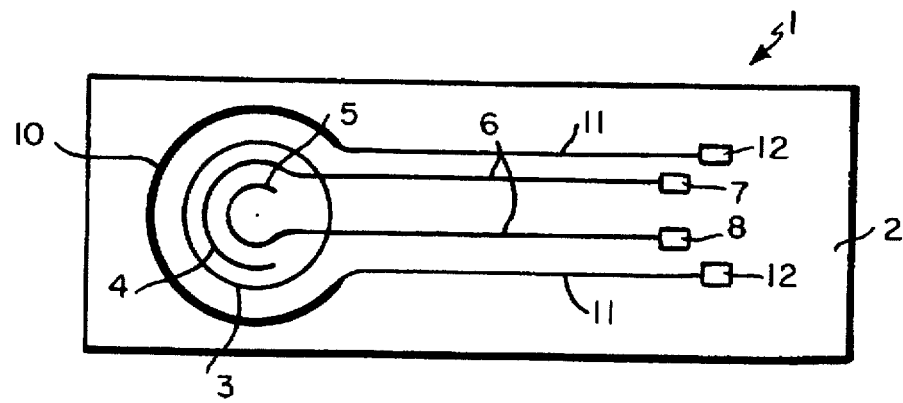

FIG. 1 illustrates an exhaust gas sensor I without a housing or attachments. The sensor comprises, in the conventional manner, a substrate 2, e.g. a carrier plate made of aluminum oxide. Onto the substrate is deposited a pad 3, with sensor material (strontium titanate etc.) applied by screen printing, and two electrodes 4 and 5 are provided. Via leads 6, electrodes 4 and 5 are connected to respective terminal pads 7 and 8, which serve for connection to an external electrical evaluation circuit (not shown).

Sensor material 3 is surrounded by a heating conductor 10, which in turn is connected via leads 11 to terminal pads 12 for electrical heating. Terminal pads 12 also serve for external electrical connection of the exhaust gas sensor.

Figure 2:
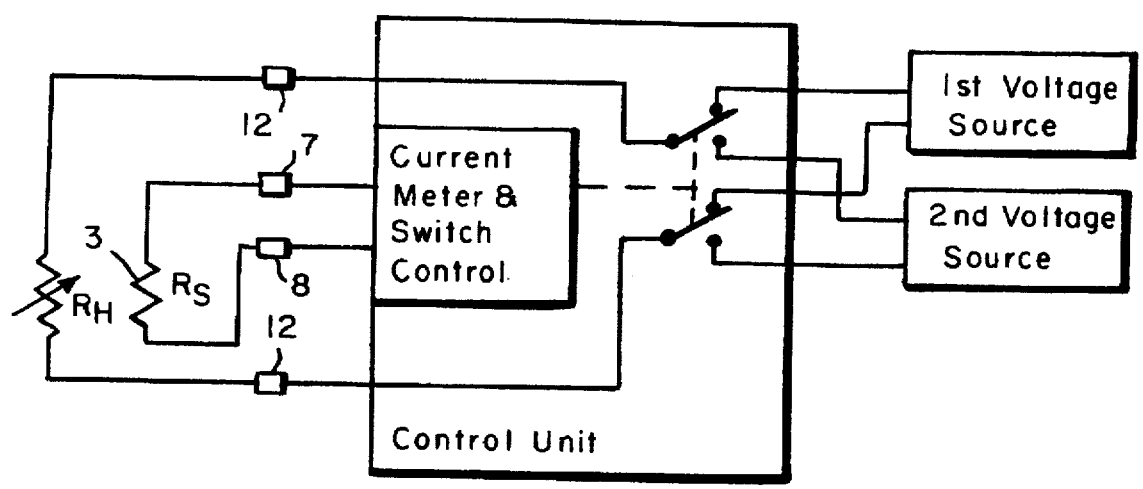

FIG. 2 illustrates a simplified equivalent circuit diagram of an exhaust gas sensor. Such a circuit is suitable for use in the sensor of the present invention.

At the terminal pads 7 and 8 of the exhaust gas sensor, with resistive sensor element 3, during operation, one can sense a resistance value $R_S$ which is characteristic of the concentration of a particular gas. At the terminal pads 12 of the electrical resistance heater 10, the electrical supply voltage for the heating of the sensor is to be applied. The electrical resistance $R_H$ of heating conductor 10 is dependent upon the temperature.

Upon a cold start of a motor vehicle, the apparatus of the invention operates as follows.

Immediately after starting the engine, the unregulated voltage of the generator/alternator (up to 30 volts in the case of a 12-volt on-board voltage) is applied to the heater 10 of the sensor. The heater's electrical resistance is small at low temperatures, so a high current flows. The heating power applied is high, and heats the sensor up correspondingly quickly. Upon reaching operating temperature, the sensor emits evaluatable signals about the exhaust gas composition. The engine control can then transition to a control mode in which the mixture composition (fuel/air) is kept in a target or command range. The exhaust gas catalytic converters can operate effectively in this range.

The time elapsed until reaching of operating temperature of the sensor is, in the planar sensor example, approximately 1 to 3 seconds. The applied heating power, at the time operating temperature is reached, has already dropped about 40%, since the resistance value $R_H$ of the heating conductor has already risen.

Then the heating device 10 is connected to the on-board network voltage of the vehicle. The applied electrical heating power is sufficient to maintain the sensor at operating temperature. The point in time for the switchover of the electrical heating applied can be determined approximately from the current drawn by heating conductor 10. The current drawn drops, when operating temperature is reached, due to the climbing resistance $R_H$, below a predetermined threshold. Alternatively, the point in time can be simply specified by lapse of a predetermined time interval after the cold start. The more temperature-independent the sensor signal is from the actual temperature of the sensor, the less critical it is to maintain a particular temperature. Correspondingly less investment for the control or regulation of the heating is therefore necessary.

The thus-far-described apparatus can lead, when used with quick-responding, electrically heated metal catalytic converters, to a substantial reduction in output of pollutants from a motor vehicle during a cold start.

In addition to use with the planar sensors of the embodiment described, the invention can also be advantageously used with conventional lambda sensors having a tubular solid electrolyte and a differently arranged electrical heater, even though the time required to reach operating temperature in such an embodiment would not be as short as that in a planar sensor having a printed heating conductor.

The second voltage source also need not operate with a lower voltage. A transition from a continuous-current mode to a pulsed-current mode would equally well reduce the heating power applied, in a suitable manner.

Those of ordinary skill in the art will appreciate that various changes and modifications are possible within the scope of the invention concept. For example, features of one embodiment could be used together with features of another embodiment. Therefore, the present invention is not limited to the particular embodiments shown and described, but rather is defined by the following claims.

What is claimed is:

1. An apparatus for determining the concentration of gas components in exhaust gas from a motor vehicle, comprising a sensor element;

an electric heater thermally coupled to said sensor element;

a voltage source supplying power to said electric heater; and a control unit controlling supply of power to said heater;

wherein
said voltage source includes at least a first voltage source and a second voltage source, said control unit controlling which one of said first and second voltage sources is applied to said heater at each instant; and one of said first and second voltage sources being directly connected from an alternator/generator.

2. The apparatus of claim 1, wherein the second voltage source is the on-board network voltage of the motor vehicle.

3. The apparatus of claim 2, wherein said on-board network voltage is in a nominal range of about 12 to 14 volts.

4. The apparatus of claim 2, wherein said on-board network voltage is in a nominal range of about 24 to 28 volts.

5. The apparatus of claim 1, wherein said first voltage source has a voltage at least 30% higher than a nominal voltage of the second voltage source.

6. The apparatus of claim 5, wherein the first voltage source is a generator/alternator of the motor vehicle.

7. The apparatus of claim 6, wherein, immediately after a cold start, said first voltage source is applied to said heater.

8. The apparatus of claim 1, wherein, after said sensor element has reached a predetermined minimum operating temperature, as indicated by current drawn by said heater, said second voltage source is applied to said heater.

9. The apparatus of claim 1, wherein a switchover, from application of said first voltage source to said heater to application of said second voltage source to said heater, is carried out upon expiration of a predetermined period of time after a cold start.

10. The apparatus of claim 1, wherein a switchover, from application of said first voltage source to said heater to application of said second voltage source to said heater, is carried out, depending upon temperature of said sensor element.

11. The apparatus of claim 1, wherein a switchover, from application of said first voltage source to said heater to application of said second voltage source to said heater, is carried out, depending upon temperature of said heater, as indicated by current drawn by said heater.

12. The apparatus of claim 1, wherein a switchover, from application of said first voltage source to said heater to application of said second voltage source to said heater, is carried out, depending upon current drawn by said sensor element.

13. The apparatus of claim 1, wherein said heater includes a heated conductor whose electrical resistance rises as its temperature rises.

14. The apparatus of claim 13, wherein said conductor consists essentially of a metal selected from the group consisting of platinum, ruthenium, rhodium, palladium, osmium, iridium, and alloys thereof.

15. The apparatus of claim 1, wherein said sensor element and said heater are located on a common substrate.

16. A method of operating an exhaust gas sensor having an associated heater in a motor vehicle equipped with a combustion engine and first and second voltage sources, said first source having a nominal voltage higher than that of said second source, comprising the steps of
applying said first voltage source to said heater for a limited period of time after starting said combustion engine; and one of said first and second voltage sources being directly connected from an alternator/generator.

17. The method of claim 16, wherein, after expiration of said limited period of time, said second voltage source, having a lower nominal voltage, is applied to said heater.

18. The method of claim 17, wherein switchover from said first voltage source to said second voltage source is carried out between 2.5 seconds and 20 seconds after a cold start.

19. The method of claim 17, wherein switchover from said first voltage source to said second voltage source is carried out between 1 second and 2.5 seconds after a cold start.

20. The method of claim 17, wherein switchover from said first voltage source to said second voltage source is carried out between 3 seconds and 10 seconds after a cold start.

21. The method of claim 20, wherein switchover from said first voltage source to said second voltage source is carried out between 5 seconds and 10 seconds after a cold start.

22. The method of claim 16, wherein switchover from said first voltage source to said second voltage source is carried out at a time which is a function of current drawn by said heater as measured by a control unit which senses said current drawn.

* * * * *